(12) United States Patent
Matsubara

(10) Patent No.: US 10,494,598 B2
(45) Date of Patent: *Dec. 3, 2019

(54) OBSERVATION IMAGE CAPTURING AND EVALUATION DEVICE, METHOD, AND PROGRAM

(71) Applicant: FUJIFILM Corporation, Tokyo (JP)

(72) Inventor: Kenta Matsubara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 15/044,560

(22) Filed: Feb. 16, 2016

(65) Prior Publication Data

US 2016/0160170 A1 Jun. 9, 2016

Related U.S. Application Data

(63) Continuation of application No. PCT/JP2014/004244, filed on Aug. 20, 2014.

(30) Foreign Application Priority Data

Aug. 22, 2013 (JP) .................................. 2013-172381
Aug. 18, 2014 (JP) .................................. 2014-165788

(51) Int. Cl.
*G06K 9/00* (2006.01)
*G02B 21/02* (2006.01)
(Continued)

(52) U.S. Cl.
CPC ............ *C12M 41/46* (2013.01); *C12M 41/36* (2013.01); *G02B 21/025* (2013.01); *G02B 21/14* (2013.01);
(Continued)

(58) Field of Classification Search
None
See application file for complete search history.

(56) References Cited

U.S. PATENT DOCUMENTS 5,969,855 A * 10/1999 Ishiwata .............. G02B 21/367
359/370
7,907,769 B2 * 3/2011 Sammak ............ G06K 9/00127
382/133
(Continued)

FOREIGN PATENT DOCUMENTS

JP 2004-348104 A 12/2004
JP 2007-222073 A 9/2007
(Continued)

OTHER PUBLICATIONS

Sammak et al (High Content Analysis of Human Embryonic Stem Cell Growth and Differentiation).*
(Continued)

*Primary Examiner* — Nancy Bitar
(74) *Attorney, Agent, or Firm* — Sughrue Mion, PLLC

(57) ABSTRACT

An observation image capturing and evaluation device includes an imaging unit that captures an image of a cell and acquires an observation image, an evaluation unit that evaluates the observation image, and a maturity information acquisition unit that acquires information related to the maturity of the cell. The imaging unit changes a method for capturing the observation image on the basis of the information related to the maturity.

13 Claims, 10 Drawing Sheets

(51) Int. Cl.
    *G06T 7/00*         (2017.01)
    *C12M 1/34*       (2006.01)
    *G02B 21/14*      (2006.01)
    *G02B 21/36*      (2006.01)
    *H04N 5/225*      (2006.01)
    *H04N 5/235*      (2006.01)

(52) U.S. Cl.
    CPC ......... *G02B 21/365* (2013.01); *G06K 9/0014* (2013.01); *G06T 7/0012* (2013.01); *H04N 5/2256* (2013.01); *H04N 5/2353* (2013.01)

(56) References Cited

U.S. PATENT DOCUMENTS

| | | | |
|---|---|---|---|
| 8,189,900 B2* | 5/2012 | Sammak | G06K 9/00127 |
| | | | 382/133 |
| 9,535,001 B2* | 1/2017 | Kuninori | C12M 41/36 |
| 9,600,874 B2* | 3/2017 | Fujimoto | G06T 7/0012 |
| 2007/0177255 A1 | 8/2007 | Kanegasaki et al. | |
| 2012/0122143 A1* | 5/2012 | Mimura | C12M 41/14 |
| | | | 435/29 |
| 2012/0322152 A1* | 12/2012 | Raghunath | C12N 5/0068 |
| | | | 435/369 |
| 2013/0236081 A1* | 9/2013 | Nakamura | G06K 9/00147 |
| | | | 382/133 |
| 2016/0160170 A1* | 6/2016 | Matsubara | C12M 41/36 |
| | | | 435/287.1 |
| 2017/0061618 A1* | 3/2017 | Matsubara | C12Q 1/02 |
| 2017/0073630 A1* | 3/2017 | Matsubara | C12M 1/34 |

FOREIGN PATENT DOCUMENTS

| | | |
|---|---|---|
| JP | 2007-295826 A | 11/2007 |
| JP | 2011-229409 A | 11/2011 |
| JP | 2011-229410 A | 11/2011 |
| JP | 2011-229411 A | 11/2011 |
| JP | 2011-229413 A | 11/2011 |
| JP | 4852890 B2 | 1/2012 |
| JP | 2012-095627 A | 5/2012 |
| WO | 2011/013319 A1 | 2/2011 |
| WO | WO 2015/182396 | * 12/2015 |

OTHER PUBLICATIONS

9. High Content Analysis of Human Embryonic Stem Cell Growth and Differentiation 205 Paul J. Sammak, Vivek Abraham, Richik Ghosh, Jeff Haskins, Esther Jane, Patti Petrosko, Teresa M. Erb, Tia N. Kinney,Feb. 2017.*

Bahnson alfred et al "Automated measurement of cell motility and proliferation" BMC Cell Biology Biomed central London Apr. 14, 2005 ; XP021001254 (Year: 2005).*

Communication dated Aug. 9, 2016, from the Japanese Patent Office in counterpart application No. 2014-165788.

Written Opinion of the International Searching Authority of PCT/JP2014/004244 dated Jan. 6, 2015.

International Search Report of PCT/JP2014/004244 dated Jan. 6, 2015.

* cited by examiner

FIG. 2

| TIME ELAPSED (MATURITY) | INITIAL STAGE OF SEEDING | STAGE AFTER LAPSE OF A FEW DAYS FROM SEEDING | STAGE AFTER LAPSE OF A WEEK FROM SEEDING |
|---|---|---|---|
| COLONY SEEDING | MEASUREMENT BY PHASE CONTRAST MICROSCOPE<br>SEPARATION OF DIFFERENT TYPES OF CELLS<br>EXTRACTION OF COLONY<br>DETERMINATION BASED ON UNIFORMITY OF STEM CELL AND SHAPE OF COLONY<br>WEIGHT  UNIFORMITY :LARGE  SHAPE OF COLONY :SMALL | MEASUREMENT BY PHASE CONTRAST MICROSCOPE<br>SEPARATION OF DIFFERENT TYPES OF CELLS<br>EXTRACTION OF COLONY<br>DETERMINATION BASED ON UNIFORMITY OF STEM CELL AND SHAPE OF COLONY<br>WEIGHT  UNIFORMITY :LARGE  SHAPE OF COLONY :MEDIUM | MEASUREMENT BY DIFFERENTIAL INTERFERENCE MICROSCOPE<br>SEPARATION OF DIFFERENT TYPES OF CELLS<br>EXTRACTION OF COLONY<br>DETERMINATION BASED ON SHAPE OF COLONY, UNIFORMITY OF BRIGHTNESS, AND UNIFORMITY OF THICKNESS<br>WEIGHT  CIRCULARITY: SMALL  APPROXIMATION OF OUTWARD SHAPE OF CELL TO COMBINATION PATTERN OF A PLURALITY OF CIRCLES: LARGE  INTERNAL DEFECT: LARGE  UNIFORMITY OF BRIGHTNESS: LARGE  UNIFORMITY OF THICKNESS: LARGE |
| SINGLE STEM CELL SEEDING | MEASUREMENT BY PHASE CONTRAST MICROSCOPE<br>DETERMINATION BASED ON UNIFORMITY OF STEM CELL AND SHAPE OF COLONY<br>WEIGHT  UNIFORMITY :LARGE  SHAPE OF COLONY :SMALL | MEASUREMENT BY PHASE CONTRAST MICROSCOPE<br>SEPARATION OF DIFFERENT TYPES OF CELLS<br>EXTRACTION OF COLONY<br>DETERMINATION BASED ON UNIFORMITY OF STEM CELL AND SHAPE OF COLONY<br>WEIGHT  UNIFORMITY :LARGE  SHAPE OF COLONY :MEDIUM | MEASUREMENT BY PHASE CONTRAST MICROSCOPE<br>SEPARATION OF DIFFERENT TYPES OF CELLS<br>EXTRACTION OF COLONY<br>DETERMINATION BASED ON SHAPE OF COLONY, UNIFORMITY OF BRIGHTNESS, AND UNIFORMITY OF THICKNESS<br>WEIGHT  CIRCULARITY: SMALL  APPROXIMATION OF OUTWARD SHAPE OF CELL TO COMBINATION PATTERN OF A PLURALITY OF CIRCLES: LARGE  INTERNAL DEFECT: LARGE  UNIFORMITY OF BRIGHTNESS: LARGE  UNIFORMITY OF THICKNESS: LARGE |
| THERE ARE DIFFERENT TYPES OF CELLS | | | |

FIG. 3

| TIME ELAPSED (MATURITY) | INITIAL STAGE OF SEEDING | STAGE AFTER LAPSE OF A FEW DAYS FROM SEEDING | STAGE AFTER LAPSE OF A WEEK FROM SEEDING |
|---|---|---|---|
| COLONY SEEDING | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT — UNIFORMITY: LARGE; SHAPE OF COLONY: SMALL | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT — UNIFORMITY: LARGE; SHAPE OF COLONY: MEDIUM | MEASUREMENT BY DIFFERENTIAL INTERFERENCE MICROSCOPE<br><br>SEPARATION OF DIFFERENT TYPES OF CELLS<br><br>EXTRACTION OF COLONY<br><br>DETERMINATION BASED ON SHAPE OF COLONY, UNIFORMITY OF BRIGHTNESS, AND UNIFORMITY OF THICKNESS<br><br>WEIGHT — CIRCULARITY: SMALL; APPROXIMATION OF OUTWARD SHAPE OF CELL TO COMBINATION PATTERN OF A PLURALITY OF CIRCLES: LARGE; INTERNAL DEFECT: LARGE; UNIFORMITY OF BRIGHTNESS: LARGE; UNIFORMITY OF THICKNESS: LARGE |
| SINGLE STEM CELL SEEDING | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT — UNIFORMITY: LARGE; SHAPE OF COLONY: SMALL | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT — UNIFORMITY: LARGE; SHAPE OF COLONY: MEDIUM | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON SHAPE OF COLONY<br><br>WEIGHT — CIRCULARITY: SMALL; APPROXIMATION OF OUTWARD SHAPE OF CELL TO COMBINATION PATTERN OF A PLURALITY OF CIRCLES: LARGE; INTERNAL DEFECT: LARGE |
| THERE ARE NO DIFFERENT TYPES OF CELLS | | | |

FIG. 4

| TIME ELAPSED (MATURITY) | INITIAL STAGE OF SEEDING | STAGE AFTER LAPSE OF A FEW DAYS FROM SEEDING | STAGE AFTER LAPSE OF A WEEK FROM SEEDING |
|---|---|---|---|
| | MEASUREMENT BY PHASE CONTRAST MICROSCOPE | MEASUREMENT BY PHASE CONTRAST MICROSCOPE | MEASUREMENT BY PHASE CONTRAST MICROSCOPE |
| | | SEPARATION OF DIFFERENT TYPES OF CELLS | SEPARATION OF DIFFERENT TYPES OF CELLS |
| | | EXTRACTION OF COLONY | EXTRACTION OF COLONY |
| | DETERMINATION BASED ON UNIFORMITY OF STEM CELL AND SHAPE OF COLONY | DETERMINATION BASED ON UNIFORMITY OF STEM CELL AND SHAPE OF COLONY | DETERMINATION BASED ON SHAPE OF COLONY |
| | WEIGHT   UNIFORMITY :LARGE   SHAPE OF COLONY :SMALL | WEIGHT   UNIFORMITY :LARGE   SHAPE OF COLONY :SMALL | CIRCULARITY: SMALL |
| | | | WEIGHT   APPROXIMATION OF OUTWARD SHAPE OF CELL TO COMBINATION PATTERN OF A PLURALITY OF CIRCLES: LARGE |
| | | | INTERNAL DEFECT: LARGE |
| SINGLE STEM CELL SEEDING | EXCHANGE OF CULTURE MEDIUM AND ADDITION OF DRUGS | | |
| THERE ARE NO DIFFERENT TYPES OF CELLS | | | |

STEM CELL

COLONY   STEM CELL

STEM CELL

COLONY

FIG. 12

| TIME ELAPSED (MATURITY) | INITIAL STAGE OF SEEDING | STAGE AFTER LAPSE OF A FEW DAYS FROM SEEDING | STAGE AFTER LAPSE OF A WEEK FROM SEEDING |
|---|---|---|---|
| OPTICAL SYSTEM OF IMAGING DEVICE | PHASE CONTRAST MICROSCOPE | PHASE CONTRAST MICROSCOPE | DIFFERENTIAL INTERFERENCE MICROSCOPE |
| OPTICAL MAGNIFICATION | HIGH | HIGH | LOW |
| RESOLUTION | HIGH | HIGH | LOW |
| EXPOSURE TIME | LONG | LONG | SHORT |
| AMOUNT OF EXPOSURE | LARGE | LARGE | SMALL |
| WAVELENGTH OF ILLUMINATION LIGHT | SHORT | SHORT | LONG |

OBSERVATION IMAGE CAPTURING AND EVALUATION DEVICE, METHOD, AND PROGRAM

CROSS-REFERENCE TO RELATED APPLICATIONS

This application is a Continuation of PCT International Application No. PCT/JP2014/004244 filed on Aug. 20, 2014, which claims priority under 35 U.S.C. § 119(a) to Japanese Patent Application No. 2013-172381 filed on Aug. 22, 2013 and Japanese Patent Application No. 2014-165788 filed on Aug. 18, 2014. Each of the above applications is hereby expressly incorporated by reference, in its entirety, into the present application.

BACKGROUND OF THE INVENTION

1. Field of the Invention

The present invention relates to an observation image capturing and evaluation device and method and a program which capture an image of a cell to acquire an observation image and evaluate the observation image.

2. Description of the Related Art

A pluripotent stem cell, such as an ES cell or an iPS cell, has the capability to be differentiated to cells of various tissues and has drawn attention since it can be applied to, for example, regenerative medicine, the development of drugs, and the interpretation of disease.

The stem cell is seeded in a scaffolding material (culture bed) in a culture container which is provided in a cell culture device and is multiplied in the scaffolding material using a culture medium (culture fluid) as nourishment. The multiplied stem cells are grown as a stem cell colony while being repeatedly agglutinated and combined with each other.

In the growth process of the stem cell, once the stem cell starts to be differentiated to a certain tissue, it is difficult to change and grow the stem cell to a different tissue while the stem cell is being differentiated. Therefore, it is important to multiply the stem cell to a sufficient number of stem cells while maintaining the stem cells in an undifferentiated state and to differentiate the stem cells to a target tissue in the subsequent process, in terms of productivity.

There is a technique which cuts out only the region which is less likely to be undifferentiated in a stem cell colony and transplants the cut region to another culture container to perform subculturing. However, when the subculturing is performed, it is necessary to extract only the undifferentiated stem cell. That is, when the stem cell is cultured, it is necessary to appropriately determine the differentiation and undifferentiation of the stem cell.

For example, JP2012-95627A and JP2011-229410A disclose a technique which captures an image of a stem cell over time, checks a change in the observation image over time, and determines the undifferentiation and differentiation of the stem cell.

JP4852890B discloses a technique which determines the undifferentiation and differentiation of a stem cell, using tens of types of feature amounts including, for example, the number of stem cells and the number of nucleoli.

In addition to the above-mentioned stem cell undifferentiation and differentiation evaluation techniques, for example, a method has been proposed which captures an image of a cell obtained by inducing a stem cell to be differentiated to a target tissue, such as a cardiac muscle or a skin, or a cancer cell, with a microscope, checks the characteristics of the image, and evaluates the cultured state of the cell.

SUMMARY OF THE INVENTION

However, when the undifferentiation and differentiation of the stem cell are determined as described in JP2012-95627A, JP2011-229410A, and JP4852890B, for example, the distribution state of the stem cell or the shape of the stem cell colony is changed with the growth of the stem cell from the start of seeding. Therefore, in some cases, even if an observation image is captured by the same imaging method, it is difficult to appropriately acquire the feature amounts used to determine the undifferentiation and differentiation of the stem cell.

Specifically, for example, in some cases, stem cell colonies are stacked in a three-dimensional direction depending on the culture conditions of the stem cell when the stem cell colonies mature. As such, when an observation image is captured by the phase contrast microscope with the stem cell colonies being stacked, a diffracted light component and a refractive light component from the stacked stem cells overlap each other. As a result, it is difficult to separate diffracted light from one stem cell and the light intensity of the entire image increases. Therefore, it is difficult to measure the micro-characteristics of each stem cell in the stem cell colony.

The invention has been made in view of the above-mentioned problems and an object of the invention is to provide an observation image capturing and evaluation device and method and a program which capture an observation image capable of appropriately evaluating cells even when the cells mature and are stacked as described above.

According to an aspect of the invention, there is provided an observation image capturing and evaluation device including: an imaging unit that captures an image of a cell and acquires an observation image; a cell evaluation unit that evaluates the observation image; and a maturity information acquisition unit that acquires information related to the maturity of a cell. The imaging unit changes a method for capturing the observation image on the basis of the information related to the maturity.

In the observation image capturing and evaluation device according to the above-mentioned aspect of the invention, the imaging unit may change a method for illuminating the cell to change the method for capturing the observation image.

The imaging unit may change the capture of an image by a phase contrast microscope and the capture of an image by a differential interference microscope to change the method for capturing the observation image.

The imaging unit may change imaging conditions of an optical system to change the method for capturing the observation image.

The imaging unit may change an optical magnification of the optical system to change the method for capturing the observation image.

The imaging unit may change an amount of exposure of the optical system to change the method for capturing the observation image.

The imaging unit may change a wavelength of illumination light to change the method for capturing the observation image.

The imaging unit may change imaging conditions of an imaging element to change the method for capturing the observation image.

The imaging unit may change an exposure time of the imaging element to change the method for capturing the observation image.

The imaging unit may change a resolution of the imaging element to change the method for capturing the observation image.

The imaging unit may change the method for capturing the observation image, on the basis of culture conditions of the cell.

The cell evaluation unit may change a method for evaluating the observation image, with the change in the method for capturing the observation image.

According to another aspect of the invention, there is provided an observation image capturing and evaluation method including: when an image of a cell is captured and an observation image is acquired and evaluated, acquiring information related to a maturity of the cell; and changing a method for capturing the observation image on the basis of the acquired information related to the maturity.

According to still another aspect of the invention, there is provided an observation image capturing and evaluation program that causes a computer to function as: a control unit that controls an imaging unit which captures an image of a cell and acquires an observation image; a cell evaluation unit that evaluates the observation image; and a maturity information acquisition unit that acquires information related to a maturity of the cell. The control unit changes a method for capturing the observation image in the imaging unit on the basis of the information related to the maturity.

According to the observation image capturing and evaluation device, method, and program according to the invention, when the image of a cell is captured and an observation image is acquired and evaluated, information related to the maturity of the cell is acquired and a method for capturing the observation image is changed on the basis of the information related to the maturity. An imaging method is changed from a method for capturing an image using a phase contrast microscope to a method for capturing an image using a differential interference microscope having a high measurement performance in a thickness direction. According to this structure, even when the cells mature and are stacked, it is possible to effectively capture the thickness or outward feature amounts and to appropriately evaluate the state of the cell such as the undifferentiation and differentiation of the cell.

BRIEF DESCRIPTION OF THE DRAWINGS

FIG. 2 is a table illustrating an example of an undifferentiation and differentiation evaluation method corresponding to the maturity and culture conditions of a stem cell.

FIG. 3 is a table illustrating an example of the undifferentiation and differentiation evaluation method corresponding to the maturity and culture conditions of the stem cell.

FIG. 4 is a table illustrating an example of the undifferentiation and differentiation evaluation method corresponding to the maturity and culture conditions of the stem cell.

FIG. 12 is a table illustrating an example of an imaging method corresponding to the maturity of a stem cell.

DESCRIPTION OF THE PREFERRED EMBODIMENTS

Figure 1:
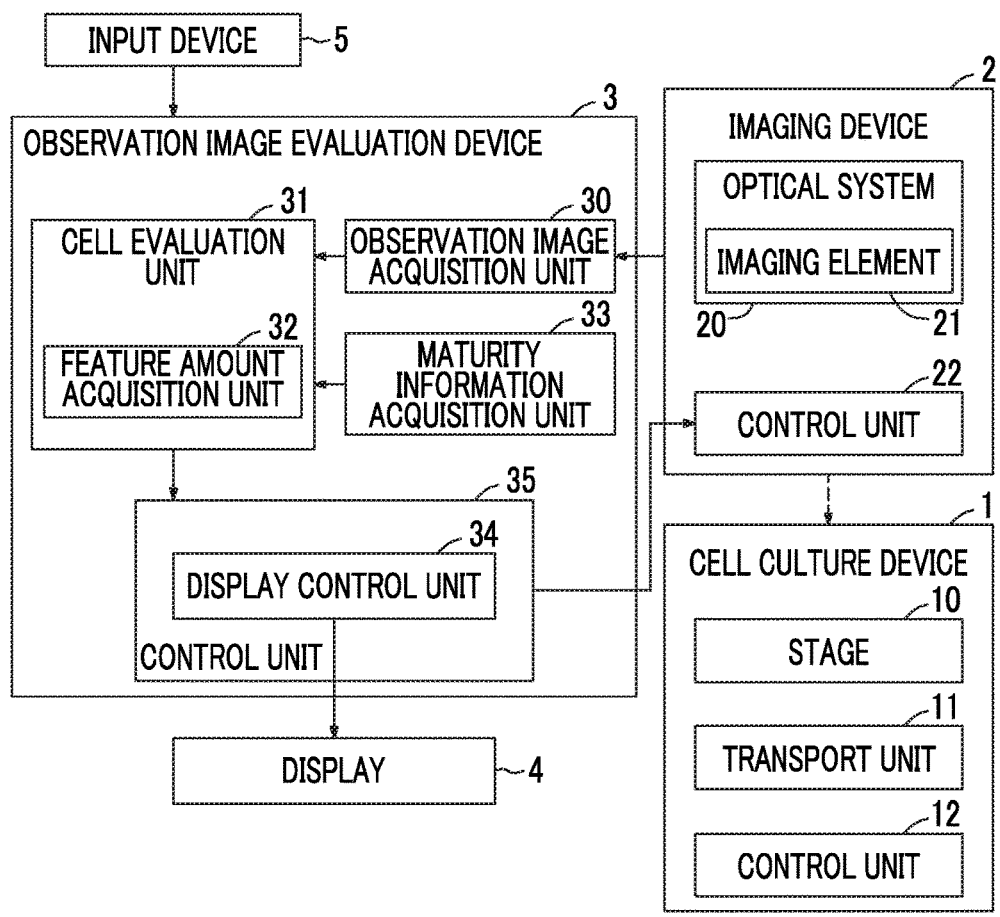
FIG. 1 is a block diagram schematically illustrating the structure of a cell culture observation system using a first embodiment of an observation image capturing and evaluation device according to the invention.

Hereinafter, an embodiment of an observation image capturing and evaluation device and method and a program according to the invention will be described in detail with reference to the drawings. The invention is characterized in a cell observation image capture method. First, the overall structure of a cell culture observation system including an embodiment of the observation image capturing and evaluation device according to the invention will be described. FIG. 1 is a block diagram schematically illustrating the structure of the cell culture observation system.

As illustrated in FIG. 1, the cell culture observation system according to this embodiment includes a cell culture device 1, an imaging device 2, an observation image evaluation device 3, a display 4, and an input device 5. In this embodiment, the imaging device 2 corresponds to an imaging unit and the observation image capturing and evaluation device is formed by the imaging device 2 and a cell evaluation unit 31 and a maturity information acquisition unit 33 of the observation image evaluation device 3.

The stem cell culture device 1 is used to culture cells. Examples of the cell to be cultured include pluripotent stem cells, such as iPS cells or ES cells, nerve cells, skin cells, cardiac muscle cells, and liver cells which are differentiation-induced from stem cells, and cancer cells. The cell culture device 1 includes a plurality of culture containers in which the cells to be cultured are seeded in a culture medium. The cell culture device 1 includes a stage 10, a transport unit 11, and a control unit 12.

The culture container whose image is to be captured by the imaging device 2 is placed on the stage 10. The transport unit 11 selects the culture container whose image is to be captured from a plurality of culture containers which are accommodated at predetermined positions in the cell culture device 1 and transports the selected culture container to the stage 10. The control unit 12 controls the overall operation of the cell culture device 1 and controls environmental conditions, such as temperature, humidity, and $CO_2$ concentration, in the cell culture device 1, in addition to the operation of the stage 10 or the transport unit 11. A known structure can be used to adjust the temperature, humidity, and $CO_2$ concentration.

The imaging device 2 captures the observation image of an observation region including the cell in the culture container placed on the stage 10. The imaging device 2 includes an optical system 20 which forms and acquires the observation image and a control unit 22 which controls the optical system 20.

The optical system 20 includes a phase contrast microscope and a differential interference microscope. The capture of the observation image by the phase contrast microscope and the capture of the observation image by the differential interference microscope are switched according to the culture maturity of the stem cell in the culture container. The switching between the imaging operations of the microscopes will be described in detail below.

These microscopes include an imaging element 21 such as a complementary metal-oxide semiconductor (CMOS) sensor or a charge-coupled device (CCD) sensor. The captured observation image of the cell is output from the imaging element 21.

The control unit 22 controls the overall operation of the imaging device 2. Particularly, in this embodiment, the control unit 22 controls, for example, the switching between the capture of the observation image by the phase contrast microscope and the capture of the observation image by the differential interference microscope, the optical magnification of the optical system 20, the exposure time or resolution of the imaging element 21, the amount of light emitted from an illumination light source which is provided in the optical system 20, or the switching between the wavelengths of illumination light. The control unit 22 changes an imaging method, depending on the maturity of the cell, on the basis of a control signal output from a control unit 35 of the observation image evaluation device 3, which will be described in detail below. For the switching between the capture of the observation image by the phase contrast microscope and the capture of the observation image by the differential interference microscope, for example, the position where the culture container is provided may be switched to the imaging position of the phase contrast microscope and the imaging position of the differential interference microscope.

An embodiment of an observation image evaluation program according to the invention is installed in a computer to implement the observation image evaluation device 3.

The observation image evaluation device 3 includes, for example, a central processing unit, a semiconductor memory, and a hard disk and an embodiment of the observation image capturing and evaluation program according to the invention is installed in the hard disk. When the control unit 35 including a central processing unit executes the program, an observation image acquisition unit 30, the cell evaluation unit 31, the maturity information acquisition unit 33, and a display control unit 34 illustrated in FIG. 1 operate.

The observation image acquisition unit 30 acquires the observation image captured by the imaging device 2 and stores the acquired observation image. In addition, the observation image acquisition unit 30 outputs the acquired observation image to the cell evaluation unit 31 and the display control unit 34.

The cell evaluation unit 31 evaluates, for example, the state of the cell on the basis of the observation image acquired by the observation image acquisition unit 30. In this embodiment, the cell evaluation unit 31 evaluates the undifferentiation and differentiation of the stem cell.

The cell evaluation unit 31 includes a feature amount acquisition unit 32 which acquires various feature amounts from the observation image and evaluates the undifferentiation and differentiation of the stem cell, on the basis of the feature amounts acquired by the feature amount acquisition unit 32. In addition, the cell evaluation unit 31 changes a method for evaluating the undifferentiation and differentiation of the stem cell, depending on the maturity of the stem cell or the culture conditions of the stem cell. Here, a change in the evaluation method means, for example, a change in evaluation criteria used to evaluate undifferentiation and differentiation or a change in a weight on each evaluation criterion when undifferentiation and differentiation are evaluated using a plurality of evaluation criteria.

In this embodiment, the cell evaluation unit 31 changes the undifferentiation and differentiation evaluation method, depending on maturity which is divided into three stages, that is, an initial stage of the seeding of the stem cell, a stage after a few days have elapsed since the seeding of the stem cell, and a stage after a week has elapsed since the seeding of the stem cell.

Information related to the maturity of the stem cell may be any information as long as it indicates the stage of the maturity of the cell. For example, a culture period which is measured by a timer can be acquired as the information related to the maturity. In addition, the information related to the maturity is not limited to the culture period. For example, the following information may be acquired as the information related to the maturity: the image information of a cell colony region in the cell image is analyzed to measure the size of the cell colony, the number of cells in the cell colony, or the number of cells in a unit area smaller than the cell colony and maturity increases as the measured number of cells increases. For example, the area, peripheral length, and maximum diameter of the cell colony can be acquired as the size of the cell colony.

For example, the brightness of the image of the cell colony region or texture, such as uniformity or roughness, may be acquired as the information related to the maturity. For example, when the cell whose image is to be captured is a stem cell, the density of the stem cells increases as the maturity of the stem cell increases. In addition, the stem cells are stacked and the brightness of the image increases gradually. Therefore, as the brightness increases, the maturity increases.

When the maturity increases and the stem cells are multiplied and stacked, the uniformity of the image increases and a smooth image with little unevenness is obtained. Therefore, the maturity increases as the uniformity of the image increases or the image becomes smoother. A known method can be used as a method for acquiring feature amounts, such as the uniformity and smoothness of the image.

The feature amounts of the shape of a stem cell colony may be acquired as the information related to the maturity. When the maturity of the stem cell increases, the shape of the stem cell colony becomes gradually similar to a circle and the differentiation of a peripheral portion of the stem cell progresses, which results in an increase in the complexity of the edge. Therefore, the feature amounts of a change in the shape of the stem cell colony can be acquired as the information related to the maturity.

In addition, the feature amounts of the thickness of the stem cell colony may be acquired as the information related to the maturity. As the maturity of the stem cell increases, the thickness of the stem cell colony increases gradually. Therefore, the feature amounts of the thickness of the stem cell colony can be acquired as the information related to the maturity. The thickness of the stem cell colony may be measured by a measurement device which is separately provided or the user may set and input the thickness of the stem cell colony, using the input device 5.

In addition, the user may set and input the passage number of the cell as the information related to the maturity, using the input device 5.

The maturity information acquisition unit 33 acquires the information related to the maturity of the cell and acquires the stage of the maturity of the cell from the information.

In this embodiment, the maturity is divided into three stages as described above. However, the maturity is not limited to three stages and may be divided into two stages or four or more stages. In addition, various gaps may be set between the stages according to, for example, culture conditions.

In this embodiment, the cell evaluation unit 31 acquires, as the culture conditions, the condition of whether different types of cells are cultured and the condition of whether a seeding method is a colony seeding method which seeds each colony or a single cell seeding method which seeds each stem cell.

When a stem cell is cultured, in some cases, a cell that is a different type from the stem cell to be cultured is used. The stem cell is grown in different ways when different types of stem cells are cultured and when the stem cell is cultured without a different type of cell. In addition, while the stem cell is being cultured, in some cases, the culture media are exchanged and drugs are added. In this case, the type of culture medium to be exchanged or the type of drug varies, depending on whether different types of cells are cultured or the stem cell is cultured without a different type of cell, and the state of the stem cell which is being cultured. In addition, a method for growing the stem cell varies depending on the culture conditions. Therefore, it is preferable to change the criteria for evaluating undifferentiation and differentiation.

For this reason, in this embodiment, the cell evaluation unit 31 acquires the condition of whether different types of cells are cultured and the condition of whether the exchange of the culture medium and the addition of drugs are performed and changes the undifferentiation and differentiation evaluation method, depending on these conditions. In addition, the cell evaluation unit 31 may acquire conditions, such as the type of culture medium to be exchanged during culture and the type of drug to be added, and may change the undifferentiation and differentiation evaluation method, depending on these conditions.

When a stem cell is cultured, there are the following stem cell seeding method: a colony seeding method which seeds each colony; and a single cell seeding method which seeds each stem cell. In the colony seeding method and the single cell seeding method, different image processing methods are used to extract feature amounts used to evaluate undifferentiation and differentiation and the stem cell is grown in different ways. Therefore, it is preferable to change the criteria for evaluating undifferentiation and differentiation. For this reason, in this embodiment, the cell evaluation unit 31 acquires the conditions of the seeding method and changes the undifferentiation and differentiation evaluation method, depending on the acquired conditions of the seeding method.

The user may set and input the above-mentioned culture conditions using the input device 5 and the cell evaluation unit 31 may acquire the input culture conditions. In addition, the culture conditions are not limited to the above-mentioned culture conditions. For example, other culture conditions which affect the progress of the growth of the stem cell, such as information about the type of culture medium or scaffold, may be used.

The feature amount acquisition unit 32 acquires feature amounts which correspond to the evaluation criteria in each evaluation method corresponding to the maturity of the stem cell or the culture conditions.

Next, each evaluation method corresponding to each stage of the maturity of the stem cell and the culture conditions will be described in detail with reference to the tables illustrated in FIGS. 2 to 4.

First, the evaluation methods corresponding to each stage of the maturity when the culture conditions are that different types of cells are cultured and the seeding method is the colony seeding method will be described with reference to FIG. 2.

First, when the maturity of the stem cell is in the initial stage of seeding, the phase contrast microscope of the imaging device 2 is used to capture an observation image and the feature amount acquisition unit 32 performs image processing for separating a stem cell colony from a different type of cells and extracting the stem cell colony in the observation image. Since the difference in size between the different type of cells and the stem cell colony is an order unit, edge detection or pattern matching can be performed to separate the stem cell colony from a different type of cells and to extract only the stem cell colony.

In this stage, the cell evaluation unit 31 evaluates undifferentiation and differentiation, using the shape of the extracted stem cell colony and the uniformity of each stem cell in the stem cell colony as the evaluation criteria.

Specifically, the feature amount acquisition unit 32 extracts an outer circumferential shape and an internal defect as information about the shape of the stem cell colony. In general, when the stem cell is not differentiated, the shape of the stem cell colony is close to a circle. When the differentiation of the stem cell progresses, the stem cell is separated and the circular shape of the stem cell colony is broken. Therefore, the degree of circularity of the outer circumferential shape of the stem cell colony can be evaluated to evaluate the undifferentiation and differentiation of the stem cell colony. In addition, the internal defect of the stem cell colony is, for example, a hole which is formed in the stem cell colony by differentiation.

The feature amount acquisition unit 32 acquires the distribution state of each stem cell in the stem cell colony and acquires information indicating the uniformity of the distribution of each stem cell. When the stem cells are uniformly distributed, the stem cells are likely to be undifferentiated. When the stem cells are distributed so as to be concentrated on a portion and the distribution of the stem cells is not uniform, the stem cells are likely to be differentiated.

The distribution state of each stem cell in the stem cell colony may be acquired by detecting the pattern of nucleoli in the stem cell or by detecting the pattern of halo which occurs due to diffracted light passing between the stem cells. When illumination light passes between the stem cells, diffraction occurs. When the distance (slit gap) between the stem cells is an integer multiple of the wavelength of the illumination light, the phases of diffracted light (positive and negative first-order diffracted light) and direct light (zeroth-order diffracted light) are synthesized and an artifact with high brightness is generated. The artifact with high brightness is halo.

Then, the cell evaluation unit 31 calculates an evaluation value related to the degree of circularity of the outer circumferential shape of the stem cell colony, an evaluation value related to whether there is an internal defect or the size of the internal defect, an evaluation value related to the uniformity of each stem cell in the stem cell colony. Then, the cell evaluation unit 31 weights the evaluation values and adds the weighted evaluation values to calculate a final evaluation value for evaluating undifferentiation and differentiation. When the evaluation value is equal to or greater than a predetermined threshold value, the cell evaluation unit 31 evaluates that the stem cell has not been differentiated. When the evaluation value is less than the threshold value, the cell evaluation unit 31 evaluates that the stem cell has been differentiated. In this case, a weight on the evaluation value related to the uniformity of the stem cell is greater than a weight on the evaluation value related to the shape of the stem cell colony (the outer circumferential shape and the internal defect).

Figure 5:
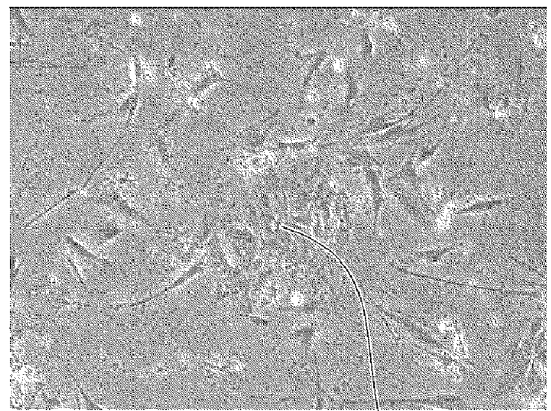
FIG. 5 is a diagram illustrating an example of an observation image of a stem cell in an initial stage of seeding.

The reason is as follows. When the maturity of the stem cell is in the initial stage of seeding, as illustrated in FIG. 5, the maturity of the stem cell colony is low. Therefore, in some cases, the outer circumferential shape of the stem cell colony is not a circle or a gap which is not related to differentiation is formed between the stem cells in the stem cell colony. Therefore, the weight on the evaluation of the uniformity of the distribution of the stem cells is greater than the weight on the evaluation of the shape of the stem cell colony, in order to accurately evaluate undifferentiation and differentiation.

When the maturity of the stem cell is in the stage after a few days have elapsed since the seeding, similarly to the initial stage of seeding, the phase contrast microscope is used to capture an observation image and the feature amount acquisition unit 32 performs image processing for extracting a stem cell colony from the observation image.

Then, in this stage, the cell evaluation unit 31 evaluates undifferentiation and differentiation, using the shape of the extracted stem cell colony and the uniformity of each stem cell in the stem cell colony as evaluation criteria. However, the weight is different from that in the initial stage of seeding.

Specifically, in this stage, the cell evaluation unit 31 sets weights on the evaluation values such that a weight on the evaluation value of the uniformity of the stem cell is greater than a weight on the evaluation value of the shape of the stem cell colony. In this case, the weight on the evaluation value of the shape of the stem cell colony is greater than the weight on the evaluation value of the shape of the stem cell colony in the initial stage of seeding.

Figure 6:
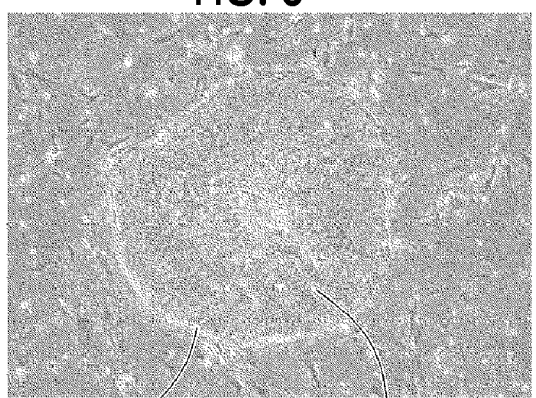
FIG. 6 is a diagram illustrating an example of the observation image of the stem cell in a stage after a few days have elapsed since the seeding.

The reason is considered as follows. In the stage after a few days have elapsed since the seeding, as illustrated in FIG. 6, the maturity of the stem cell colony increases slightly, the outer circumferential shape of the stem cell colony is close to a circle, and the density of the stem cells in the stem cell colony increases. Therefore, the weight on the evaluation value of the shape of the stem cell colony increases in order to accurately evaluate undifferentiation and differentiation.

When the maturity of the stem cell is in the stage after a week has elapsed since the seeding, the imaging device 2 captures an observation image, using not the phase contrast microscope, but the differential interference microscope, and the feature amount acquisition unit 32 performs image processing for separating a different type of cells from the stem cell colony in the observation image and extracting the stem cell colony.

Figure 7:
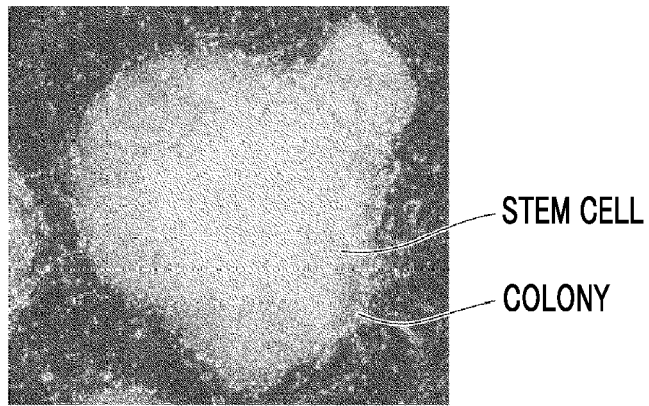
FIG. 7 is a diagram illustrating an example of the observation image of the stem cell in a stage after a week has elapsed since the seeding.

In this stage, in some cases, the growth of the stem cell colony is developed and the stem cells are stacked as illustrated in FIG. 7. As such, when the stem cells are stacked, a diffracted light component and a refracted light component from the stacked stem cells overlap each other. As a result, it is difficult to separate diffracted light from one stem cell and the light intensity of the entire image increases. Therefore, it is difficult to measure the micro-characteristics of each stem cell in the stem cell colony with the phase contrast microscope. For this reason, in this stage, as described above, the observation image is captured by the differential interference microscope.

In this stage, the cell evaluation unit 31 evaluates undifferentiation and differentiation, using the shape of the stem cell colony, the uniformity of the brightness of the stem cell colony, and the uniformity of the thickness of the stem cell colony as the evaluation criteria.

Specifically, the feature amount acquisition unit 32 extracts the outer circumferential shape and internal defect of the stem cell colony, similar to the previous stage. In addition, the feature amount acquisition unit 32 acquires the distribution of the brightness signal in the stem cell colony and acquires the uniformity of the brightness signal. Furthermore, the feature amount acquisition unit 32 acquires the uniformity of the thickness of the stem cell colony. The thickness of the stem cell colony can be measured by an interferometer such as optical coherence tomography (OCT).

For example, the standard deviation of the brightness signal or the thickness may be acquired as the uniformity of the brightness signal or the thickness, or the difference between the maximum value and the minimum value may be acquired as the uniformity of the brightness signal or the thickness. When the brightness signal or the thickness is uniformly distributed, the stem cell is likely to be undifferentiated. When portions with a higher or lower brightness than the surroundings or portions with a larger or smaller thickness than the surroundings are non-uniformly distributed so as to be concentrated, the stem cell is likely to be differentiated.

The cell evaluation unit 31 calculates an evaluation value related to the degree of circularity of the outer circumferential shape of the stem cell colony, an evaluation value related to the approximation of the outer circumferential shape to a combination pattern of a plurality of circles, an evaluation value related to whether there is an internal defect or the size of the internal defect, an evaluation value related to the uniformity of brightness, and an evaluation value related to the uniformity of the thickness, weights the evaluation values, and adds the weighted evaluation values to calculate a final evaluation value for evaluating undifferentiation and differentiation. The approximation of the outer circumferential shape to a combination pattern of a plurality of circles means the degree of approximation between the outer circumferential shape of the stem cell colony and a combination pattern of a plurality of circles.

In this case, for the weights on each evaluation value, the weight on the evaluation value related to the degree of circularity is relatively small and the weights on the evaluation values related to the approximation of the outer circumferential shape to a combination pattern of a plurality of circles, the internal defect, the uniformity of the brightness, and the uniformity of the thickness are relatively large.

Figure 8:
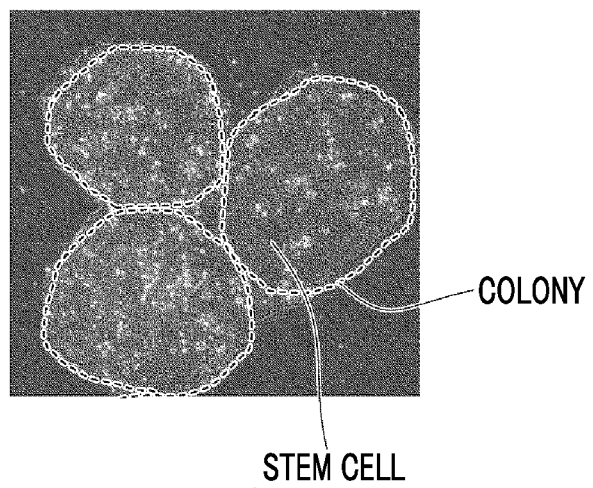
FIG. 8 is a diagram illustrating an example of the observation image of the stem cell in the stage after a week has elapsed since the seeding.

When the maturity of the stem cell is in the stage after a week has elapsed since the seeding, in some cases, the stem cell colonies are combined with each other and the outer circumferential shape of the stem cell colony is not maintained in a circle, as illustrated in FIG. 8. For this reason, the weight on the evaluation value related to the degree of circularity is set to a small value and the weight corresponding to, for example, the evaluation value related to the approximation of the outer circumferential shape to a combination pattern of a plurality of circles is set to a large value, which makes it possible to accurately evaluate undifferentiation and differentiation.

The evaluation method corresponding to each maturity stage when the culture conditions are that different types of cells are cultured and the cell colony seeding method is used has been described above.

Next, an evaluation method corresponding to each maturity stage when the culture conditions are that different types of cells are cultured and the single cell seeding method is used will be described with reference to FIG. 2.

In this case, in the single cell seeding method, only the evaluation method when the maturity of the stem cell is in the initial stage of seeding differs from that in the colony seeding method, and the evaluation method when the maturity of the stem cell is the stage after a few days have elapsed since the seeding and the evaluation method when the maturity of the stem cell is the stage after a week from seeding are the same as those in the colony seeding method.

When different types of cells are cultured and the single cell seeding method is used, an observation image is captured by the phase contrast microscope, similarly to the colony seeding method. However, in this case, since no colony has been formed in the initial stage of seeding, image processing for extracting the colony is not performed, unlike the colony seeding method.

Then, similarly to the colony seeding method, the feature amount acquisition unit 32 extracts the outer circumferential shape and internal defect of the stem cell colony. However, in this stage, the colony is not clearly formed, as described above. Therefore, the feature amount acquisition unit 32 specifies the region in which the stem cell colony is estimated to be formed from the distribution state of the stem cells and extracts the outer circumferential shape and internal defect of the specified region.

In addition, the feature amount acquisition unit 32 acquires the distribution state of a different type of cells and the stem cells and acquires the uniformity of the distribution of these cells. In this case, since it is difficult to distinguish the stem cell from a different type of cells, the uniformity of both cells is acquired.

Then, the cell evaluation unit 31 calculates an evaluation value related to the degree of circularity of the outer circumferential shape of the stem cell colony, an evaluation value related to whether there is an internal defect or the size of the internal defect, and an evaluation value related to the uniformity of the stem cell and the different type of cells, weights the evaluation values, and adds the weighted evaluation values to calculate a final evaluation value for evaluating undifferentiation and differentiation. In this case, the weight on the evaluation value related to the uniformity of the stem cell is greater than the weight on the evaluation value related to the thickness of the stem cell colony (the outer circumferential shape and the internal defect).

The upper part of FIG. 3 illustrates the evaluation method corresponding to each maturity stage when the culture conditions are that the stem cell is cultured without a different type of cells and the colony seeding method is used. In this case, the evaluation methods corresponding to all of the maturity stages are the same as those when different types of cells are cultured and the colony seeding method is used.

The lower part of FIG. 3 illustrates the evaluation method corresponding to each maturity stage when the stem cell is cultured without a different type of cells and the single cell seeding method is used. In this case, the evaluation method when the maturity of the stem cell is in the initial stage of seeding and the evaluation method when the maturity of the stem cell is in the stage after a few days have elapsed since the seeding are the same as those when the different types of cells are cultured and the single cell seeding method is used, and only the evaluation method when the maturity of the stem cell is in the stage after a week has elapsed since the seeding is different from that when the different types of cells are cultured and the single cell seeding method is used.

Specifically, when the stem cell is cultured without a different type of cells and the single cell seeding method is used, in the stage after a week has elapsed since the seeding, an observation image is not captured by the differential interference microscope, but is captured by the phase contrast microscope. The feature amount acquisition unit 32 performs image processing for separating the stem cell colony from a different type of cells and extracting the stem cell colony in the observation image.

Figure 9:
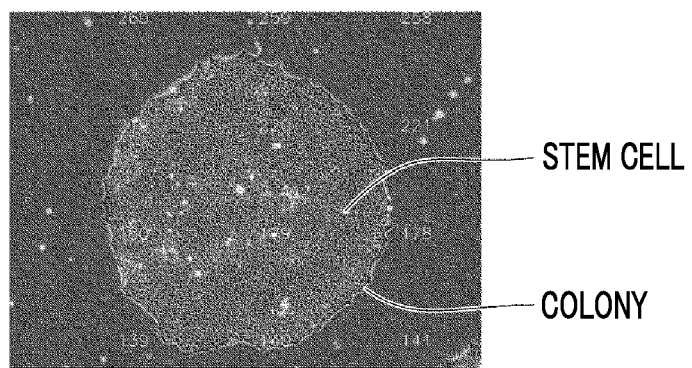
FIG. 9 is a diagram illustrating an example of the observation image when a stem cell colony is grown so as to extend in a plane direction.

The reason why the cell image is not captured by the differential interference microscope, but is captured by the phase contrast microscope is as follows. When different types of cells are cultured, in some cases, the stem cells are stacked by the growth of the stem cell colony. When the stem cell is cultured without a different type of cells and the single cell seeding method is used, it takes a lot of time until the stem cells are stacked. For a period of about a week, as illustrated in FIG. 9, the stem cell colony is grown so as to extend in the plane direction. When the step cell is cultured without a different type of cells and the colony seeding method is used, the stem cell colony is grown earlier than that when the single cell seeding method is used and the stem cells are likely to be stacked. For this reason, the cell image is captured by the differential interference microscope as described above.

Then, the cell evaluation unit 31 weights the evaluation value related to the degree of circularity of the outer circumferential shape of the stem cell colony, the evaluation value related to the approximation of the outer circumferential shape to a combination pattern of a plurality of circles, and the evaluation value related to whether there is an internal defect or the size of the internal defect and adds the weighted evaluation values to calculate a final evaluation value for evaluating undifferentiation and differentiation. However, the calculation of the evaluation value related to the uniformity of brightness and the uniformity of thickness is not considered. For the weight on each evaluation value, similarly to the case in which different types of cells are cultured, the evaluation value related to the degree of circularity is relatively small and the evaluation values related to the approximation of the outer circumferential shape to a combination pattern of a plurality of circles and the internal defect are relatively large.

FIG. 4 illustrates the evaluation method corresponding to each maturity stage when the culture conditions are that the step cell is cultured without a different type of cells, the single cell seeding method is used, and the exchange of the culture medium and the addition of drugs are performed before a few days have elapsed since the seeding of the stem cell.

In the case of the culture conditions, the evaluation method in the initial stage of seeding and the evaluation method in the stage after a week has elapsed since the seeding are the same as those when the stem cell is cultured without a different type of cells, the single cell seeding method is used, and the culture medium and the addition of drugs are not performed. When the exchange of the culture medium and the addition of drugs are performed after a few days have elapsed since the seeding, undifferentiation and differentiation are evaluated, on the basis of the same evaluation criteria as those in the initial stage of seeding, in order to evaluate the effect obtained by the addition of the drugs using the same evaluation criteria as those in the evaluation method before the drugs are added.

The undifferentiation and differentiation evaluation method of the cell evaluation unit 31 according to this embodiment has been described above.

Returning to FIG. 1, the display control unit 34 displays the observation image acquired by the observation image acquisition unit 30 on the display 4 or displays the evaluation result of undifferentiation and differentiation by the cell evaluation unit 31 on the display 4. The display control unit 34 may display the feature amounts or the evaluation values used for evaluation as well as the evaluation result on the display 4.

The control unit 35 controls the overall operation of the observation image evaluation device 3 and outputs a control signal to the control unit 22 of the imaging device 2 such that an observation image capture method is changed depending on information related to the maturity acquired by the maturity information acquisition unit 33.

The input device 5 includes, for example, a mouse or a keyboard and receives an operation input by the user. For example, the input device 5 receives the setting or change of the evaluation criteria for evaluating undifferentiation and differentiation or receives the setting or change of the weights used to calculate the evaluation values.

Figure 10:
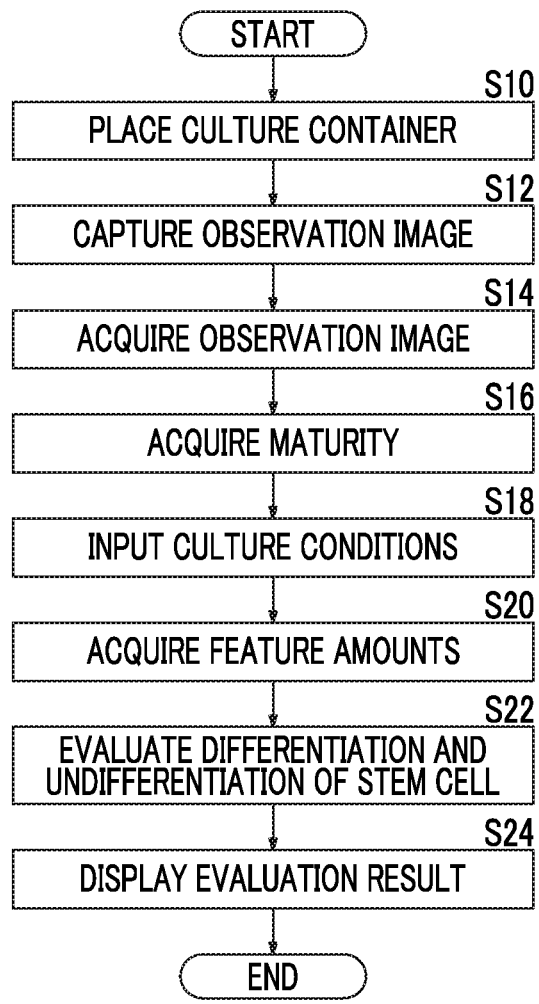
FIG. 10 is a flowchart illustrating the operation of the cell culture observation system illustrated in FIG. 1.

Next, the operation of the cell culture observation system will be described with reference to the flowchart illustrated in FIG. 10.

First, in the cell culture device 1, the transport unit 11 selects the culture container whose image is to be captured from a plurality of culture containers provided in the cell culture device 1 and the selected culture container is placed on the stage 10 (S10).

Figure 11:
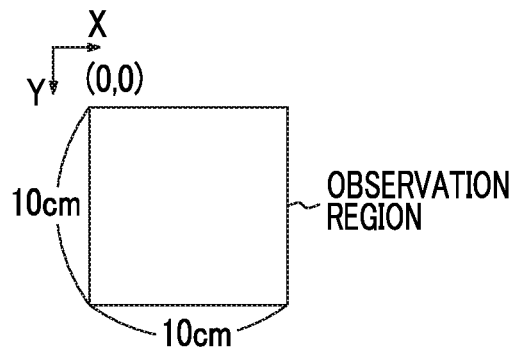
FIG. 11 is a diagram illustrating an example of an observation region.

Then, the observation image of an observation region including the stem cell in the culture container is captured by the phase contrast microscope or the differential interference microscope of the imaging device 2 (S12). Specifically, 40 shots×40 shots of images of a rectangular observation region with a size of 10 cm×10 cm illustrated in FIG. 11 are captured by the phase contrast microscope to acquire one cell image.

Then, the observation image captured by the imaging device 2 is output to the observation image evaluation device 3 and is then acquired by the observation image acquisition unit 30 of the observation image evaluation device 3 (S14).

In this case, the maturity information acquisition unit 33 acquires, for example, the culture period at the time when the observation image is captured as the information related to the maturity (S16) and culture conditions are input by the user through the input device 5 (S18).

Then, the observation image acquired by the observation image acquisition unit 30, the information related to the maturity acquired by the maturity information acquisition unit 33, and the culture conditions input by the user are output to the cell evaluation unit 31 and the feature amount acquisition unit 32 acquires feature amounts corresponding to the maturity and the culture conditions, on the basis of the input observation image, maturity information, and culture conditions (S20).

Then, the cell evaluation unit 31 evaluates the undifferentiation and differentiation of the stem cell in the observation image on the basis of the feature amounts acquired by the feature amount acquisition unit 32, using an evaluation method corresponding to the maturity and culture conditions of the stem cell (S22).

The evaluation result of undifferentiation and differentiation by the cell evaluation unit 31 is output to the display control unit 34 and the display control unit 34 displays the input observation image and the input evaluation result of undifferentiation and differentiation on the display 4 (S24).

The cell culture observation system according to the above-described embodiment acquires the captured observation image of the stem cell, acquires information related to the maturity of the stem cell when the observation image is evaluated, and changes the method for evaluating undifferentiation and differentiation, on the basis of the information related to the maturity. Therefore, it is possible to appropriately evaluate the undifferentiation and differentiation of the stem cell in each growth stage until the stem cell is grown to a certain level after the seeding of the stem cell.

In addition, the method for evaluating undifferentiation and differentiation is changed depending on the culture conditions of the stem cell. Therefore, even when the culture conditions are different, it is possible to appropriately evaluate the undifferentiation and differentiation of the stem cell.

The evaluation criteria used to evaluate undifferentiation and differentiation are not limited to, for example, the uniformity of the stem cell or the shape of the stem cell colony. For example, the density of the stem cells, the generation state of halo in the stem cell colony, or the definiteness of the boundary between the stem cell colonies may be used as the evaluation criteria.

In the above-described embodiment, in the initial stage of seeding and after a few days have elapsed since the seeding, the observation image is captured by the phase contrast microscope. In the stage after a week has elapsed since the seeding, the observation image is captured by the differential interference microscope. That is, the imaging method of the imaging device 2 is changed depending on the maturity of the stem cell. In addition, even in the stage after a week has elapsed since the seeding, the observation image is captured by the differential interference microscope when different types of cells are cultured, and the observation image is captured by the phase contrast microscope when the stem cell is cultured without a different type of cells and the single cell seeding method is used. That is, the imaging method of the imaging device 2 is changed depending on the culture conditions.

As such, in addition to the structure in which the type of the optical system 20 is changed depending on the maturity or the culture conditions to change the imaging method, the imaging conditions of the optical system 20 or the imaging conditions of the imaging element may be changed to change the imaging method. In addition, a change from the phase contrast microscope to the differential interference microscope also means a change in an illumination method.

Next, a case in which imaging conditions are changed depending on the maturity or culture conditions of the stem cell will be described with reference to the table illustrated in FIG. 12.

First, in the initial stage of the seeding and the stage after a few days have elapsed since the seeding, it is preferable that the optical magnification of the optical system 20 is higher than that in the stage after a week has elapsed since the seeding, in order to give a greater weight to the evaluation of the distribution state of each stem cell than to the outward shape of the stem cell colony. In this case, it is possible to capture the image of each stem cell with high accuracy. In contrast, in the stage after a week has elapsed since the seeding, the optical magnification is relatively low. In this case, it is possible to capture the image of the overall shape of the stem cell colony. Therefore, it is possible to evaluate, for example, the approximation of the outer circumferential shape of the stem cell colony to a combination pattern of a plurality of circles or the internal defect of the stem cell colony with high accuracy.

For the same reason as described above, it is preferable that the resolution of the imaging element 21 in the optical system 20 is relatively high in the initial stage of seeding and the stage after a few days have elapsed since the seeding and is relative low in the stage after a week has elapsed since the seeding. For a change in the resolution, for example, a plurality of imaging elements 21 with different resolutions may be switched or binning may be performed for downsampling when an image signal is read from one imaging element 21.

In the initial stage of seeding and the stage after a few days have elapsed since the seeding, the weight on the evaluation of the distribution state of each stem cell is greater than the weight on the evaluation of the outward shape of the stem cell colony. Therefore, it is preferable that the exposure time of the imaging element 21 is set to be longer than that in the stage after a week has elapsed since the seeding, in order to detect, for example, the edge or halo of each stem cell with high accuracy. In this case, it is possible to capture the image of each stem cell with high accuracy.

Figure 13:
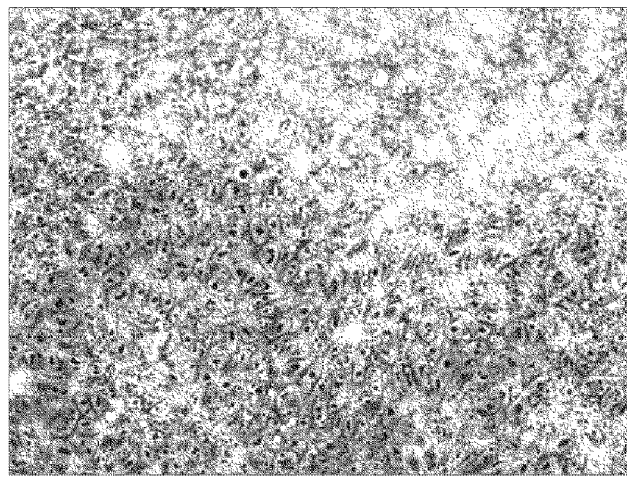
FIG. 13 is a diagram illustrating the stacked state of stem cell colonies.
Figure 14:
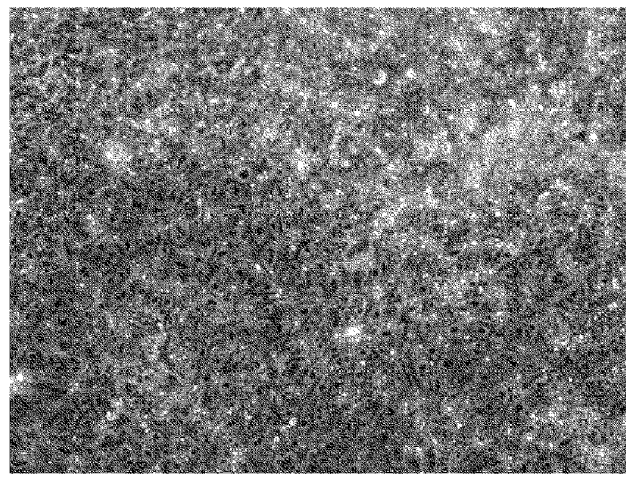
FIG. 14 is a diagram illustrating an observation image which is captured when the exposure time of the stem cell colony, of which the observation image illustrated in FIG. 13 is to be captured, is short.

In the stage after a week has elapsed since the seeding, the stem cell colonies are stacked as described above. A diffracted light component and a refracted light component from the stacked stem cells overlap each other, which results in an increase in the light intensity of the entire image. As a result, as illustrated in FIG. 13, white voids are generated in the observation image, which makes it difficult to accurately observe the state of the stem cell colony. Therefore, in the stage after a week has elapsed since the seeding, it is preferable that the exposure time of the imaging element 21 is set to a relatively small value. FIG. 14 illustrates an observation image when the exposure time of the stem cell colony, of which the cell image illustrated in FIG. 13 is to be captured, is short.

For a change in the exposure time, the number of exposures may be changed to change the exposure time. For example, in the initial stage of seeding and the stage after a few days have elapsed since the seeding, the number of exposures may be two or more and a plurality of observation images may be added. In the stage after a week has elapsed since the seeding, the number of exposures may be one and an observation may be acquired. A change in the number of exposures substantially corresponds to a change in the exposure time.

For the same reason as described above, in the initial stage of seeding and the stage after a few days have elapsed since the seeding, it is preferable that the amount of light from the light source of the optical system 20 is relatively large. In the stage after a week has elapsed since the seeding, it is preferable that the amount of light is relatively small.

In the initial stage of seeding and the stage after a few days have elapsed since the seeding, it is necessary to capture the image of the edge of each stem cell with a high resolution and the wavelength of illumination light from the optical system 20 is preferably shorter than the wavelength of illumination light in the stage after a week has elapsed since the seeding. In this case, it is possible to increase a spatial resolution. In contrast, in the stage after a week has elapsed since the seeding, the image of the overall shape of the stem cell colony is captured and extremely high spatial resolution is not required. When the wavelength of illumination light is short, strong light scattering occurs. Therefore, scattering occurs at the boundary between the stem cell and a portion which is not the stem cell and the boundary of the overall shape of the stem cell colony is blurred.

Figure 15:
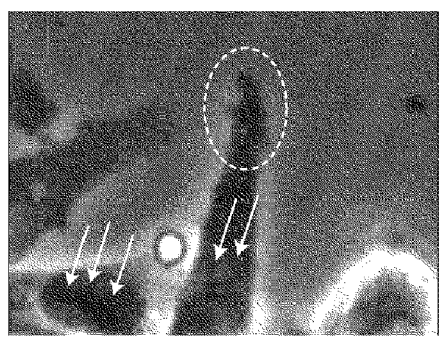
FIG. 15 is a diagram illustrating a phase-difference image which is captured by illumination light with a relatively short wavelength.
Figure 16:
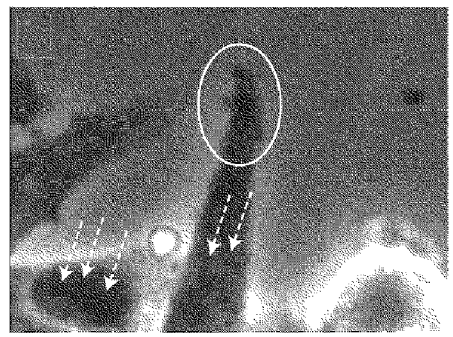
FIG. 16 is a diagram illustrating a phase-difference image which is captured by illumination light with a relatively long wavelength.

For this reason, in the stage after a week has elapsed since the seeding, it is preferable to use illumination light with a relatively long wavelength. FIG. 15 illustrates a phase-difference image which is captured by illumination light with a relatively short wavelength and FIG. 16 illustrates a phase-difference image which is captured by illumination light with a relatively long wavelength. In FIGS. 15 and 16, an arrow indicates a microstructure in the stem cell. In the observation image illustrated in FIG. 15 which is captured by illumination light with a short wavelength, the microstructure is more clearly seen than that in the cell image illustrated in FIG. 16 which is captured by illumination light with a long wavelength. In FIGS. 15 and 16, an ellipse indicates a boundary portion between the cells. As can be seen from the drawings, in the observation image illustrated in FIG. 16 which is captured by illumination light with a long wavelength, the blurring of the boundary is less than that in the cell image illustrated in FIG. 15 which is captured by illumination light with a short wavelength.

In the above-described embodiment, the method for evaluating the undifferentiation and differentiation of the stem cell has been described. However, the invention is not limited to the method for evaluating the undifferentiation and differentiation of the stem cell. For example, the degree of differentiation of a differentiation-induced cell may be evaluated or a method for evaluating, for example, the degree of malignancy of a cancer cell may be determined on the basis of information related to maturity. The morphological characteristics of the differentiation-induced cell vary depending on the type of differentiation-induced cell. Therefore, it is preferable to set an evaluation method corresponding to a change in the morphological characteristics in advance. For example, when a cardiac muscle colony is evaluated, the distribution state of each cardiac muscle cell may be evaluated in the initial stage of culture and the pulsation cycle of the cardiac muscle cell may be evaluated in the stage in which the cardiac muscle cell is grown and starts to pulsate.

When a tissue including a blood vessel is cultured, for example, the distribution state of each cell may be evaluated in the initial stage of culture and the length or state of the blood vessel may be evaluated in the stage in which the cell is grown and the formation of the blood vessel reaches a certain level.

In addition, the cell evaluation unit 31 may acquire the information about the type of cell and may determine a cell colony evaluation method on the basis of the type of cell and the information related to maturity.

As described above, the stem cells are stacked. However, the stacked cells are not limited to the stem cells. In some cases, the differentiation-induced cells are stacked by the growth of the cell colony, similarly to the stem cell. Therefore, the capture of images by the differential interference microscope and the capture of images by the phase contrast microscope may change depending on the maturity of the cell.

Similarly to the stem cell, the optical magnification of the optical system 20 may be changed or the resolution of the imaging element 21 may be changed, depending on the maturity of the differentiation-induced cell. In addition, similarly to the stem cell, the exposure time of the imaging element 21, the amount of light from the light source of the optical system 20, or the wavelength of illumination light from the optical system 20 may be changed depending on the maturity of the differentiation-induced cell.

What is claimed is:

1. An observation image capturing and evaluation device comprising:
   an imaging device that captures an observation image of cells;
   a memory; and
   a processor that is connected to the memory and that is configured to:
      acquire information related to a maturity of the cells, wherein the information related to the maturity is a period of time from a time of seeding the cells: and
      evaluate undifferentiation and differentiation of the cells using the observation image, according to evaluation criteria of the cells corresponding to the maturity of the cells and a culture condition of the cells,
   wherein the imaging device includes a phase contrast microscope and a differential interference microscope,
   wherein, in a case in which the maturity progresses, the imaging device changes from imaging by the phase contrast microscope to imaging by the differential interference microscope, and
   wherein, in a case in which the maturity is in an initial stage of seeding, the processor performs a process of extracting a cell colony from the observation image when the culture condition is a colony seeding method of seeding the cells by cell colony and estimates the cell colony from the cells in the observation image when the culture condition is a single cell seeding method of seeding the cells by cell.

2. The observation image capturing and evaluation device according to claim 1,
   wherein the imaging device changes a method for illuminating the cells to change the method for capturing the observation image.

3. The observation image capturing and evaluation device according to claim 1, wherein the imaging device changes imaging conditions of an optical system to change the method for capturing the observation image.

4. The observation image capturing and evaluation device according to claim 3, wherein the imaging device changes an optical magnification of the optical system to change the method for capturing the observation image.

5. The observation image capturing and evaluation device according to claim 3, wherein the imaging device changes an amount of exposure of the optical system to change the method for capturing the observation image.

6. The observation image capturing and evaluation device according to claim 3, wherein the imaging device changes a wavelength of illumination light to change the method for capturing the observation image.

7. The observation image capturing and evaluation device according to claim 1, wherein the imaging device changes imaging conditions of an imaging element to change the method for capturing the observation image.

8. The observation image capturing and evaluation device according to claim 7, wherein the imaging device changes an exposure time of the imaging element to change the method for capturing the observation image.

9. The observation image capturing and evaluation device according to claim 7, wherein the imaging device changes a resolution of the imaging element to change the method for capturing the observation image.

10. The observation image capturing and evaluation device according to claim 1, wherein the imaging device changes the method for capturing the observation image, on the basis of culture conditions of the cells.

11. The observation image capturing and evaluation device according to claim 1, wherein the cell evaluation device changes a method for evaluating the observation image, with the change in the method for capturing the observation image.

12. An observation image capturing and evaluation method comprising:
   when an observation image of cells is captured by an imaging device that includes a phase contrast microscope and a differential interference microscope, acquiring information related to a maturity of the cells, wherein the information related to the maturity is a period of time from a time of seeding the cells; and
   evaluating undifferentiation and differentiation of the cells using the observation image, according to evaluation criteria of the cells corresponding to the maturity of the cells and a, culture condition of the cells,
   wherein in a case in which the maturity progresses, changing the imaging device from imaging by the phase contrast microscope to imaging by the differential interference microscope, and
   wherein, in a case in which the maturity is in an initial stage of seeding, extracting a cell colony from the observation image when the culture condition is a colony seeding method of seeding the cells by cell colony and estimates the cell colony from the cells in the observation image when the culture condition is a single cell seeding method of seeding by cell.

13. A non-transitory computer-readable recording medium having stored therein an observation image capturing and evaluation program that performs the following functions:
   controlling an imaging device which captures an observation image of cells, the imaging device including a phase contrast microscope and a differential interference microscope;
   acquiring information related to a maturity of the cells, wherein the information related to the maturity is a period of time, from a time of seeding the cells; and
   evaluating undifferentiation and differentiation of the cells using the observation image, according to evaluation criteria of the cells corresponding to the maturity of the cells and a culture condition of the cells,
   wherein in a case in which the maturity progresses, changing the imaging device from imaging by the phase contrast microscope to imaging by the differential interference microscope, and
   wherein, in a case in which the maturity is in an initial stage of seeding, extracting a cell colony from the observation image when the culture condition is a colony seeding method of seeding the cells by cell colony and estimating the cell colony from the cells in the observation image when the culture condition is a single cell seeding method of seeding the cells by cell.

* * * * *